United States Patent [19]

Stedman et al.

[11] Patent Number: 5,702,954
[45] Date of Patent: Dec. 30, 1997

[54] METHOD TO DETECT PHOSPHORUS

[75] Inventors: Donald H. Stedman, Denver; Patti A. Meeks, Westminster, both of Colo.

[73] Assignee: Colorado Seminary, Denver, Colo.

[21] Appl. No.: 536,571

[22] Filed: Sep. 29, 1995

[51] Int. Cl.$^6$ .................................................. G01N 21/76
[52] U.S. Cl. ...................... 436/103; 436/104; 436/105; 422/52
[58] Field of Search ................................ 436/103–105; 422/52, 98

[56] References Cited

U.S. PATENT DOCUMENTS

| | | | |
|---|---|---|---|
| 3,287,089 | 11/1966 | Wilburn | 23/254 |
| 3,877,819 | 4/1975 | Haas | 356/187 |
| 4,097,239 | 6/1978 | Patterson | 23/232 R |
| 4,238,199 | 12/1980 | Runham | 436/103 |
| 5,227,135 | 7/1993 | Godec et al. | 422/52 |
| 5,424,217 | 6/1995 | Benner et al. | 435/123 |

OTHER PUBLICATIONS

P.A. David and M. Novotny, "Characterization of the Nitrogen and Phosphorus Termionic Detector Response in Capillary Supercritical Fluid Chromatography," Sep. 15, 1989, pp. 2082–2086, Analytical Chemistry.

Gregory C. Turk, "Single-and Double-Resonance Laser-Induced Ionization of Phosphorus Monoxide in an Air0-Acetylene Flame for the Determination of Phosphorus," Aug. 1, 1991, pp. 1607–1611. Analytical Chemistry..

M. Pakniat, N. Maleki and A. Safavi, "Construction and design of a gas-sensing detector capable of handling and determining sulphur–and phosphorus–containing gaseous samples," 1994, pp. 225–232, Analytica Chimica Acta.

*Primary Examiner*—Lyle A. Alexander
*Attorney, Agent, or Firm*—Dorr, Carson, Sloan & Birney, P.C.

[57] ABSTRACT

An apparatus to detect and measure the amount of phosphorus in phosphorus-containing compounds comprises a burning chamber with a housing having an integral combustion chamber. A flammable reducing agent such as hydrogen is introduced into the combustion chamber along with a sample containing phosphorus admixed with air or oxygen. At least a portion of any phosphorus in the sample will be converted into phosphorus monoxide (PO) by the combustion. The resulting phosphorus monoxide is immediately drawn into a low-pressure, ambient temperature reaction chamber and reacted with ozone to convert the phosphorus monoxide to chemiluminescent phosphorus dioxide. A light-measuring device then measures the intensity of the light released from the chemiluminescent phosphorus dioxide.

5 Claims, 1 Drawing Sheet

METHOD TO DETECT PHOSPHORUS

BACKGROUND OF THE INVENTION

1. Field of the Invention

The present invention relates generally to the field of detecting phosphorus. More particularly, the present invention discloses an apparatus and method for the detection and measurement of phosphorus combustion products that have been reacted with ozone to form chemiluminescent reaction products.

2. Statement of the Problem

Phosphorus is an essential element for both plants and animals. It is found throughout the bodies of animals, especially in the bones and as pan of molecules such as phospholipids (found in cell membranes), adenosine triphosphate (ATP), DNA, and RNA. Phosphorus can also be extremely toxic to living organisms. For example, organophosphorus derivatives, are used extensively in insecticides (e.g., tetraethyl pyrophosphate), many of which are also toxic to humans. Insecticide residues are found in soil and groundwater, and the detection of these residues is important for their elimination from the environment and to protect the health of both humans and animals. Organic derivatives of phosphoric acid can also be used to make nerve gases for chemical warfare purposes. Satin, phosphine, soman, and tabun are examples of such chemical warfare agents. Nerve gases have also been used in terrorist attacks. Nerve gases are a serious threat to both troops and non-combatants as they can quickly kill and disable large numbers of people. The very rapid and specific detection of phosphorus-based nerve gases in very low amounts in the atmosphere is therefore of great interest to the military. It is also of interest to detect any residues of nerve gases in soil and water.

Specific detection of the presence and amount of phosphorus enables the respective phosphorus-containing compound to be identified and measured. Important to the specific detection of phosphorus is the nondetection of other constituents of phosphorus-containing compounds derived from living matter, that is, carbon, oxygen, hydrogen, and nitrogen.

Detection and identification of the constituents of chemical compounds is a challenging task. Many processes have been developed to detect and measure particular chemicals in samples having an unknown composition. A well-known example of such a system is the flame photometric detector. In flame photometry, a hydrogen flame produces electromagnetic radiation in the presence of air or oxygen, usually as a visible spectrum of light. The sample to be tested is first mixed with an air stream and then burned in the hydrogen flame. The luminous radiation produced by this combustion is then measured by a light detector, such as a photomultiplier tube. However, flame photometry, although somewhat selective for phosphorus, is subject to interference from other molecules during the combustion process. Possible interferents include any substance that will produce a charged ion in a hydrogen flame, such as most organic compounds. The sensitivity level of this method is also inadequate for trace analysis.

Other methods used to detect phosphorus or phosphorus-containing compounds include laser-induced ionization and thermionics. Laser-induced ionization is an expensive and complicated technique that uses a laser or laserenhanced collisions to excite and ionize phosphorus monoxide (PO) in an airacetylene flame. The sensitivity of this method for phosphorus is about 30 ng/ml.

Thermionics provides both nitrogen and phosphorus sensitivity to an otherwise insensitive flame ionization detector and is discussed in greater detail below.

Examples in the field of phosphorus detectors include the following:

| Inventor | U.S. Pat. No. | Issue Date |
|---|---|---|
| Wilburn | 3,287,089 | Nov. 22, 1966 |
| Haas | 3,877,819 | Apr. 15, 1975 |
| Patterson | 4,097,239 | June 27, 1978 |
| Benner et al. | 5,424,217 | June 13, 1995 |

David and Novotny, "Characterization of the Nitrogen and Phosphorus Thermionic Detector Response in Capillary Supercritical Fluid Chromatography," *Anal. Chem.* 1989, vol. 61, pp. 2082–2086.

Turk, "Single- and Double-Resonance Laser-Induced Ionization of Phosphorus Monoxide in an Air-Acetylene Flame for the Determination of Phosphorus," *Anal. Chem.* 1991, vol. 63, pp. 1607–1611.

Pakniat et al., "Construction and Design of a Gas-Sensing Detector Capable of Handling and Determining Sulphur- and Phosphorus-Containing Gaseous Samples," *Anal. Chim. Acta* 1994, vol. 286, pp. 225–232.

Wilburn discloses a sampler that tests air for the presence of organophosphorus compounds. The sampler utilizes the chemiluminescent reaction of luminol with the organophosphorus compounds to detect the latter. The invention is limited to the detection of organophosphorus compounds in air.

Haas teaches the detection of phosphorus by using a dual-hydrogen burner to burn a vaporous sample containing phosphorus and/or sulfur. The green emission of a phosphorus hydride and the blue emission of an unidentified phosphorus species are viewed. This technique constitutes flame emission spectrometry. The green emission most likely involves an excited state of HPO.

Patterson discloses a flame photometric detector to observe the flame emission of HPO. Two flames are used. The first, hydrogen-rich flame reduces complex chemical compounds to simpler molecules, which are subsequently combusted in a second flame to generate characteristic optical species that can be detected by conventional spectrophotometric means.

Benner et al. teach the chemiluminescent detection of sulfur compounds by the mixture of combustion products containing sulfur monoxide (SO) with ozone to form an active species ($SO_2$) that emits light as it decays to a less active state. Benner et al. neither teach nor suggest the use of this method and apparatus for the detection of phosphorus, which is in a different chemical family than sulfur, by ozone-activated chemiluminescence.

David and Novotny discuss an improvement of the thermionic detector for the detection of nitrogen and phosphorus. The thermionic detector is the current state of the art for the gas chromatographic detection of phosphorus. An alkali-metal salt (preferably rubidium oxide or cesium oxide with silicon dioxide, sodium carbonate, and boric acid) is volatilized by a hydrogen flame. The volatilized alkali-metal salt then undergoes electron transfer reactions with the phosphorus species in the flame, and these reactions can be detected. The David thermionic detector is used in conjunction with capillary supercritical fluid chromatography to provide phosphorus detection sensitivities in the picogram ($10^{-12}$) range. This detector has problems with decreased selectivity for phosphorus over carbon.

Turk discusses the use of molecular flame spectrometry for the determination of phosphorus. Two lasers are used to excite PO molecules to a high energy state in which they are ionized either by collision or by absorption of a second photon from one of the lasers. This method provided no additional sensitivity or selectivity for phosphorus detection over previous methods such as plasma emission spectroscopy.

Pakniat et al. disclose a method to determine sulfur and phosphorus by simple flame photometry. This method measures HPO and $S_2$ emissions in a reducing ($H_2$) flame. The detection limit of the method is 0.112 ng of P in a gaseous sample.

None of the above references describe a method or apparatus for accurately, simply, specifically, and sensitively detecting phosphorus in the low femtogram ($10^{-15}$) range in a fluid stream, either gaseous or liquid, that contains other components, especially carbon, hydrogen, oxygen, and nitrogen, to which the detector is not sensitive.

3. Solution to the Problem

The present invention provides a specific and sensitive method and apparatus for detecting phosphorus in a fluid or gaseous sample. A sample (e.g., from a gas or liquid chromatograph or ambient air) is mixed with air or oxygen and then directed into a burning chamber. In the burning chamber the sample is combusted in a reducing flame with an excess of reducing agent to produce gaseous combustion products. The combustion products are then directed to a light-tight and low-pressure reaction chamber by vacuum extraction. In the reaction chamber, the combustion products are reacted with ozone so that the phosphorus combustion products form an excited phosphorus dioxide ($PO_2^*$) molecule that releases light (chemiluminesces) as it returns to an unexcited state ($PO_2$). The released light passes through a filter to a light detector that measures and records the intensity of the chemiluminescence. In this way an indication of the presence and amount of phosphorus in the sample can be gained.

As described in greater detail below, the present invention utilizes a hydrogen-air flame to produce combustion products that include phosphorus monoxide (PO) for subsequent reaction with ozone to produce chemiluminescent phosphorus dioxide ($PO_2^*$). Because of its thermal instability, ozone cannot be directly introduced at the combustion site to provide the chemiluminescent reaction. The present invention utilizes a sampling probe with a narrow orifice to quickly withdraw substantially all of the combustion products to the lowpressure chamber for reaction with ozone. An important aspect of the present invention is the quenching of the chemical combustion reactions by lowering the pressure in the reaction chamber to about 1 to about 50 torr, with about 10 torr preferred. The low pressure also reduces the possibility that water vapor among the combustion products will condense in the reaction chamber.

The present invention is capable of very quickly detecting phosphorus at the femtogram ($10^{-15}$) range. Its specificity is not affected by the presence of other components often found with phosphorus from organic sources, such as carbon, hydrogen, oxygen, or nitrogen. The phosphorus detector of the present invention is simple and inexpensive to use compared with previous methods.

SUMMARY OF THE INVENTION

The present invention discloses an apparatus and method to detect and measure the amount of phosphorus in phosphorus-containing compounds. A sample that may contain phosphorus is mixed with air or oxygen. The air or oxygen is first passed through a charcoal filter to remove any contaminating phosphorus. The admixed air/sample is then directed into a combustion chamber. A flammable reducing agent, preferably hydrogen, is introduced through a port into the combustion chamber along with the air/sample mixture. Combustion of the air/sample mixture and reducing agent occurs at the end of the port where the reducing agent enters the combustion chamber. The combustion process converts at least a portion of any phosphorus in the sample into phosphorus monoxide (PO), among other combustion products such as water vapor.

The resulting combustion products are drawn by vacuum through a narrow orifice into a light-tight reaction chamber. The reaction chamber is kept at a lower pressure than the combustion chamber to prevent the condensation of the water vapor produced as a byproduct of the combustion and to quench any further chemical combustion reactions. In the reaction chamber the combustion products are reacted with ozone. This reaction with ozone converts the phosphorus monoxide in the combustion products into chemiluminescent phosphorus dioxide. The light emitted by the chemiluminescent phosphorus dioxide passes through an appropriate filter to a light-measuring device that measures and records the intensity of the light.

It is an object of the present invention to provide a method to detect phosphorus or its compounds at femtogram or higher levels in a fluid stream, and in particular from an environmental air sample or a sample from a gas or liquid chromatograph.

It is a further object of the present invention to provide a novel and improved method and apparatus for detecting phosphorus-containing compounds in a rapid and continuous manner without the detection of or interference of other compounds such as those containing carbon, hydrogen, oxygen, or nitrogen.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
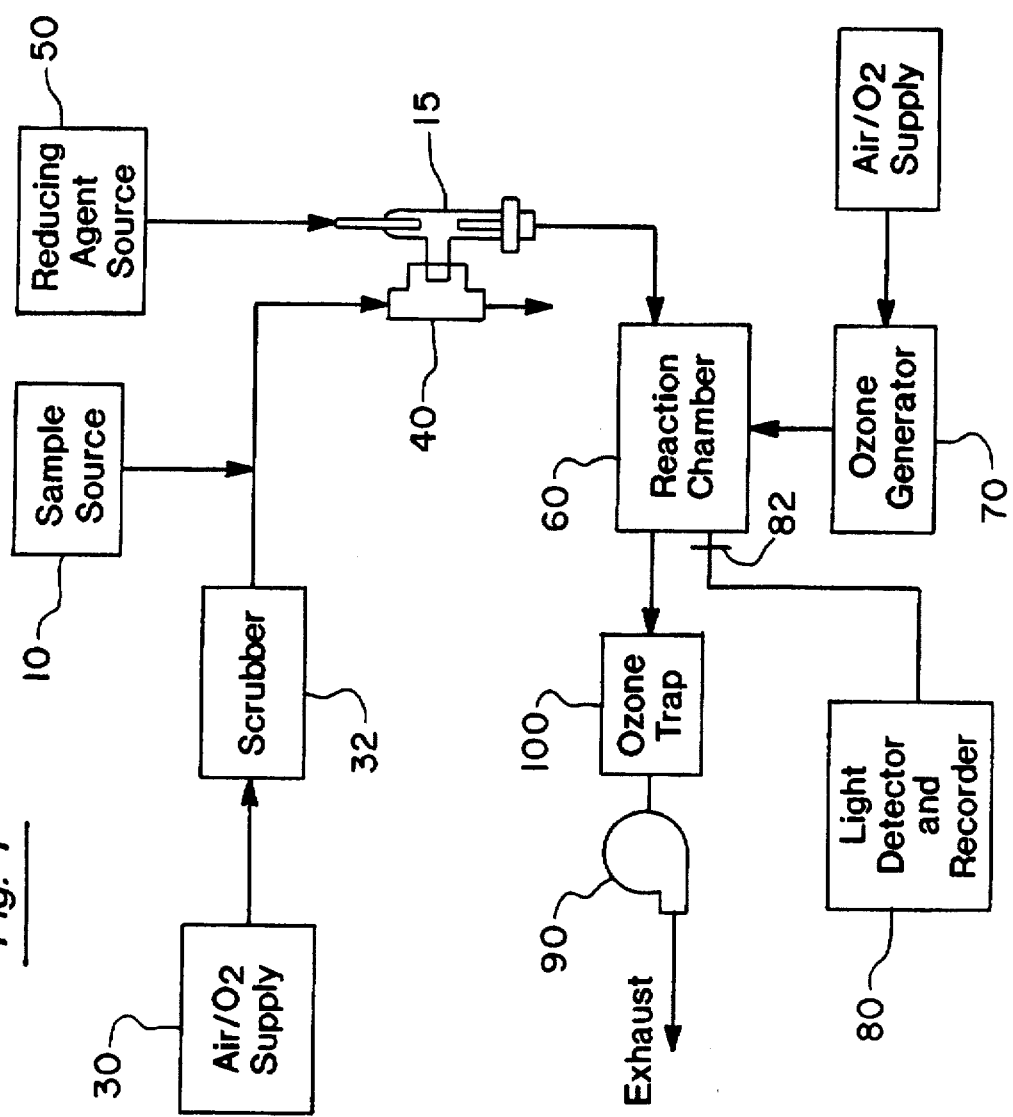
FIG. 1 is a diagram illustrating the apparatus of the present invention used to detect phosphorus.

FIG. 1 illustrates a preferred embodiment of the apparatus of the present invention. In this embodiment, a sample (either gaseous or liquid) whose phosphorus content is to be determined is directed from a source 10 to a burner assembly 15. Before reaching the burner assembly 15, the sample is admixed with oxygen, preferably from an ambient air supply 30, although pure oxygen can be used under the teachings of the present invention.

Before mixing with the sample, the air from the air supply 30 is first passed through a scrubber 32 (e.g., an activated charcoal trap) to remove any phosphorus compounds and avoid contamination of the sample. The air/sample mixture is then directed through a first arm of a T-joint 40. The base of the T-joint 40 connects with the burner assembly 15, while a second arm of the T-joint 40 is open to the ambient atmosphere to allow excess air/sample mixture to exit the system. The T-joint 40 thus serves as a vent, so the burner assembly 15 does not receive more of the air/sample mixture than can be pulled through it by a vacuum system 90. It is to be understood that the air/sample mixture is always in excess of the amount necessary to fill the burner assembly 15, so that ambient air does not enter the burner assembly 15 through the open T-joint arm. This vent may not be necessary in a system, such as a gas chromatograph, in which all flows are well controlled.

Figure 2:
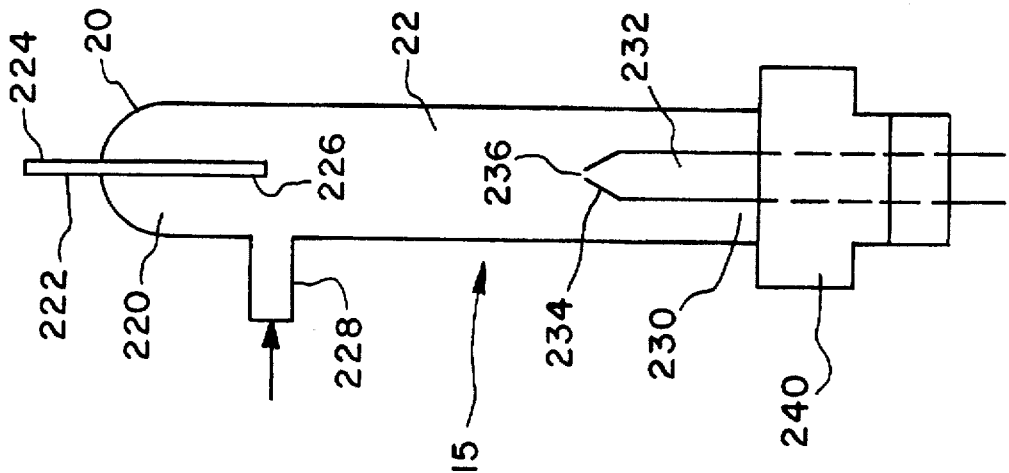
FIG. 2 is a cross section of the burner assembly of the present invention.

The burner assembly 15 is shown in greater detail in FIG. 2. A housing 20 contains an integral combustion chamber 22. The first end 220 of the housing 20 has placed therein a first port 222 having a first end 224 and a second end 226. The first end 220 of the housing 20 is further comprised of a second port 228 through which the air/sample mixture enters the integral combustion chamber 22 from the T-joint 40. The second end 230 of the housing 20 holds a probe 232 having an end 234 with a flow-restricted orifice 236. The probe 232 is formed of quartz or a similar heat-resistant and chemically inert material such as, for example, ceramic. A sliding seal 240 covers the second end 230 of the housing 20, as discussed in more detail below.

As the air/sample mixture enters the burner assembly 15 through the second port 228, it is combusted at the second end 226 of the first port 222 in the presence of a flammable reducing agent. The reducing agent enters the combustion chamber 22 through the first end 224 of the first port 22. The reducing agent is preferably hydrogen ($H_2$), although other reducing as methane, butane, propane, alcohols, aldehydes, amines, ketones, olefins, aromatic compounds, and natural gas could be substituted. If desired, before entering the combustion chamber the reducing agent may be spiked with a small amount of a halocarbon, such as carbon tetrachloride, to reduce background noise. The reducing agent is present in the combustion chamber 22 in excess over the oxygen in the air/sample mixture such that the stoichiometric ratio of hydrogen or other reducing agent to oxygen is about 1.2 to about 2.0. This results in a reducing flame for the combustion process. The reducing flame, which resides between the second end 226 of the first port 222 and the orifice 236 at the end 234 of the probe 232, converts at least a portion of the phosphorus in the air/sample mixture to phosphorus monoxide (PO).

Low pressure produced by a vacuum pump 90 or other evacuation means is used to extract substantially all of the gaseous combustion products, among which is phosphorus monoxide (PO), from the combustion chamber 22 through the orifice 236 and into a light-tight reaction chamber 60. A standard 25 liter/minute vacuum pump may be utilized in the present invention, or, if greater sample flow rates are desired, a 300 liter/minute vacuum pump may be utilized (Model 1012, Alcatel, France).

Phosphorus monoxide is a free radical. As such, it is short lived and highly reactive. The PO formed by the combustion process described above will react with other combustion products and even with other PO molecules. Therefore, the PO formed by the combustion process must be moved into the reaction chamber 60 as quickly as possible. To achieve this, the sliding seal 240 holding the probe 232 through which the PO exits the combustion chamber 22 can be adjusted along the housing 20 to place the orifice 236 at any desired distance from the second end 226 of the first port 222 in order to vary the residence time of the sample in the combustion chamber 22 from about 1 msec to about 40 msec. In addition, the size of the orifice 236 is determined empirically to produce a total flow in the range of approximately 350 to 650 $cm^3$/minute (preferably about 500 $cm^3$/minute) at a reaction chamber pressure of about 10 torr. The resulting short residence time of the PO in the combustion chamber 22 minimizes the loss of PO to subsequent reactions.

As an additional precaution against loss of the PO radical to subsequent reactions, the reaction chamber 60 is kept at ambient temperature and low pressure with respect to the combustion chamber 22. The low pressure, between about 1 and 50 torr, quenches any remaining chemical combustion reactions and also prevents the condensation of water vapor, which forms up to 25% of the combustion products. The combination of the sliding seal 240 and the low pressure in the reaction chamber allows the PO radical to be transported intact to the reaction chamber 60. As a further precaution, all the tubing between the orifice 236 and the reaction chamber 60 is coated with halocarbon wax (Series 1200, Halocarbon Products, Hackensack, N.J.) to minimize loss of PO to wall reactions.

The combustion products within the reaction chamber 60 are then admixed with ozone that is continuously directed into the reaction chamber 60 from an ozone generator 70 or other ozone source. A high-capacity ozone generator is preferably utilized that produces about 100 $cm^3$ of ozonized oxygen per minute. Excess ozone is provided to the reaction chamber 60 from the ozone generator 70 to be mixed with the combustion products. The ozone reacts with the phosphorus monoxide (PO) in the combustion products to create an excited state of phosphorus dioxide ($PO_2^*$). This excited $PO_2^*$ then chemiluminesces, giving off a photon of light, as shown in the equations below:

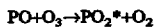

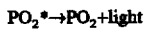

The light produced by this reaction passes through a filter 82 to a light detector 80 that converts the signal to a voltage output that is measured and recorded. The combustion products are then removed from the reaction chamber 60 by the use of the vacuum pump 90. An ozone trap 100 placed along the exhaust line captures any excess ozone to prevent contamination of the atmosphere or the vacuum pump 90.

Optionally, a filter 82 can be chosen to permit passage only of light of the wavelengths produced by the above chemiluminescent phosphorus reaction. That is, the filter only allows the passage of light having a wavelength of about 500 nm or greater. This prevents interference from other combustion products, such as sulfur monoxide, that produce chemiluminescence at wavelengths shorter than 500 nm upon reaction with ozone. Nitric oxide (NO) may also be produced by the combustion process. Nitric oxide reacts with the ozone to produce chemiluminescent nitrogen dioxide ($NO_2^*$). This $NO_2^*$ produces a deep red chemiluminesence (greater than 650 nm). To prevent the detection of the $NO_2^*$ chemiluminescence, a light detector 80 should be chosen that is not sensitive to wavelengths greater than about 600 nm. Thus, the filter eliminates chemiluminescence having wavelengths of less than about 500 nm, and the light detector 80 is insensitive to chemiluminescence having wavelengths of greater than about 600 nm.

In a second embodiment, the flame zone in the combustion chamber 22 is replaced with a heated oven. Combustion takes place on the walls of heated oven. The temperature range for combustion to occur in such a heated oven is between about 750° C. and 850° C. In an alternative embodiment, the combustion in such a heated oven occurs as follows. The sample to be tested enters the oven through a ceramic tube, preferably about 1/8 inch in outer diameter. The reducing agent is directed into the combustion zone through a ceramic tube having an outer diameter of about 1/16 inch, the terminal end of which is inserted into the 1/8-inch sample tube. Combustion occurs at the terminal end of the 1/16-inch tube inside the sample tube. The combustion products are drawn out of this combustion tube assembly and into the reaction chamber via a T-joint at the end of the 1/8-inch tube near the entry point of the reducing agent.

In another embodiment, when it is desired to analyze the phosphorus content of a liquid stream, such as results from high-performance liquid chromatography, a hot zone can be established that both vaporizes the liquid sample stream and performs the combustion reaction to generate phosphorus monoxide. For example, the stream can be directed through a capillary tube under moderate pressure and heat (e.g., 300° C. and 2000 psig). After leaving the reaction tube, the products of the combustion are allowed to return to ambient pressure and temperature, after which they are reacted with ozone.

In a further embodiment, the sample probe with orifice is used to sample the combustion products of the hydrogen flame of a flame ionization detector (FID) contained within a gas chromatograph. The combustion products are drawn through the probe, which is held inside the gas chromatograph by a sliding seal, and then transferred to the reaction chamber. In this embodiment, the flame ionization detector retains sensitivity to all the organic compounds, while the detector of the present invention singles out the phosphorus-containing species.

The above disclosure sets forth a number of embodiments of the present invention. Other arrangements or embodiments, not precisely set forth, could be practiced under the teachings of the present invention and as set forth in the following claims.

We claim:

1. A method for detecting and measuring phosphorus in phosphorus-containing compounds comprising the steps of:

admixing a sample including a phosphorus-containing compound with oxygen;

introducing said sample mixed with oxygen into a combustion chamber;

providing a flammable reducing agent into said combustion chamber to fuel combustion within said combustion chamber to convert said phosphorus in said phosphorus-containing compound to phosphorus monoxide;

extracting at least a portion of said phosphorus monoxide from said combustion chamber into a reaction chamber;

contacting said phosphorus monoxide in said reaction chamber with ozone under such conditions that said phosphorus monoxide is converted to chemiluminescent phosphorus dioxide; and measuring the intensity of said chemiluminescence to provide an indication of the amount of phosphorus present in said sample.

2. The method of claim 1 wherein said reducing agent is selected from the group consisting of hydrogen, methane, butane, and propane.

3. The method of claim 1 wherein said reducing agent is hydrogen.

4. The method of claim 1, wherein said reaction chamber is maintained at substantially ambient temperature.

5. The method of claim 1 wherein said sample has a residence time in said chamber in the range of about 1 millisecond to about 40 millisecond.

* * * * *

UNITED STATES PATENT AND TRADEMARK OFFICE
CERTIFICATE OF CORRECTION

PATENT NO. : 5,702,954
DATED : December 30, 1997
INVENTOR(S) : Stedman et al.

It is certified that error appears in the above-indentified patent and that said Letters Patent is hereby corrected as shown below:

```
Column 1, line 13, replace "as pan of" with --as part of--
Column 1, line 24, replace "Satin" with --Sarin--
Column 1, line 60, replace "therrnionics" with --thermionics--
Column 1, line 61, replace "laserenahnced" with --laser-enhanced--.
Column 1, line 63, replace "airacetylene" with --air-acetylene--.
Column 3, line 45, replace "lowpressure" with --low pressure--
Column 5, line 25, replace "reducing as methane" with --reducing
          agents such as methane--
```

Signed and Sealed this

Twenty-eighth Day of July, 1998

Attest:

BRUCE LEHMAN

*Attesting Officer*         *Commissioner of Patents and Trademarks*